(12) United States Patent
Ghosh et al.

(10) Patent No.: US 9,259,663 B2
(45) Date of Patent: Feb. 16, 2016

(54) PROCESS FOR THE PREPARATION OF NATURAL SALT FORMULATIONS FOR SEAWATER SUBSTITUTION, MINERAL FORTIFICATION

(71) Applicant: COUNCIL OF SCIENTIFIC & INDUSTRIAL RESEARCH, New Delhi (IN)

(72) Inventors: Pushpito Kumar Ghosh, Gujarat (IN); Sumesh Chandra Upadhyay, Gujarat (IN); Sandhya Chandrikaprasad Mishra, Gujarat (IN); Vadakke Puthoor Mohandas, Gujarat (IN); Divesh Narayan Srivastava, Gujarat (IN); Vinod Kumar Shahi, Gujarat (IN); Rahul Jasvantrai Sanghavi, Gujarat (IN); Sreekumaran Thampy, Gujarat (IN); Babulal Surabhai Makwana, Gujarat (IN); Imran Pancha, Gujarat (IN); Ruma Pal, Kolkata (IN); Ramkrishna Sen, Kharagpur (IN)

(73) Assignee: Council of Scientific & Industrial Research, Nel Delhi (IN)

( * ) Notice: Subject to any disclaimer, the term of this patent is extended or adjusted under 35 U.S.C. 154(b) by 79 days.

(21) Appl. No.: 14/365,896

(22) PCT Filed: Dec. 27, 2012

(86) PCT No.: PCT/IN2012/000857
§ 371 (c)(1),
(2) Date: Jun. 16, 2014

(87) PCT Pub. No.: WO2013/098857
PCT Pub. Date: Jul. 4, 2013

(65) Prior Publication Data
US 2015/0004673 A1    Jan. 1, 2015

(30) Foreign Application Priority Data
Dec. 29, 2011  (IN) .......................... 3422/DEL/2011

(51) Int. Cl.
*C01D 1/30* (2006.01)
*B01D 1/00* (2006.01)
*A23L 1/304* (2006.01)
*A23L 2/52* (2006.01)
*A01G 33/00* (2006.01)
*C01D 3/06* (2006.01)
*C01F 11/18* (2006.01)
*C01F 11/46* (2006.01)
*A23K 1/175* (2006.01)
*C12N 1/12* (2006.01)
*C12N 1/20* (2006.01)

(52) U.S. Cl.
CPC .............. *B01D 1/0035* (2013.01); *A01G 33/00* (2013.01); *A23K 1/1751* (2013.01); *A23K 1/1753* (2013.01); *A23L 1/304* (2013.01); *A23L 2/52* (2013.01); *B01D 1/0017* (2013.01); *C01D 3/06* (2013.01); *C01F 11/18* (2013.01); *C01F 11/46* (2013.01); *C12N 1/12* (2013.01); *C12N 1/20* (2013.01); *Y02W 10/37* (2015.05)

(58) Field of Classification Search
CPC ......................................................... C01D 1/30
USPC ........................................................... 23/303
See application file for complete search history.

(56) References Cited

U.S. PATENT DOCUMENTS 5,485,808 A * 1/1996 Huebner ................ A01K 63/04
119/231

* cited by examiner

*Primary Examiner* — Edward Johnson
(74) *Attorney, Agent, or Firm* — Abelman, Frayne & Schwab

(57) ABSTRACT

The present invention relates to natural crude salt formulations arid their cost-effective preparation. In particular, the invention discloses the fractionation of seawater into three fractions which can thereafter be suitably combined to reconstitute seawater in its pristine form for its various applications such as growth of marine microbes, flora and fauna in a marine environment, especially where such environments have to be created in locations far removed from the sea and/or where there is a requirement to modify the composition of seawater to better its performance. The fractions can also be blended appropriately to exclude the major constituent, namely sodium chloride, and thereby be useful for mineralization/re-mineralization of waters which are deficient in mineral nutrients such as calcium, magnesium, potassium, sulphate and bicarbonate including rain water and desalinated waters obtained through thermal/RO desalination. The invention can be practiced most cost-effectively in solar salt works operated on sea brine.

14 Claims, 4 Drawing Sheets

PROCESS FOR THE PREPARATION OF NATURAL SALT FORMULATIONS FOR SEAWATER SUBSTITUTION, MINERAL FORTIFICATION

CROSS-REFERENCE TO RELATED APPLICATIONS

This application is a National Phase of PCT/IN2012/000857, filed 27 Dec. 2012, which claims priority from Indian Application No. 3422/DEL/2011, filed 29 Dec. 2011, the disclosures of which are all incorporated herein by reference.

FIELD OF THE INVENTION

The present invention relates to a process for the preparation of natural salt formulations for seawater substitution, mineral fortification. More particularly, the invention relates to solar evaporation of seawater and its fractionation into three parts which can be suitably mixed to obtain desired solid compositions. These solid formulations are suitable for easy transportation and usable in aquariums, culturing of marine algae/microbes, and also other marine applications which demand use of seawater and particularly where seawater is not available in the vicinity, on the one hand, and fortification of low TDS (total dissolved solids) water and related applications, on the other hand.

BACKGROUND OF INVENTION

Seawater is a storehouse of chemicals and contains more than 73 elements in dissolved state. Coastal locations have abundant seawater whereas landlocked areas do not have seawater. Yet seawater may be required in the latter areas too for diverse purposes. Since transporting seawater is a costly and difficult proposition, many efforts have been made to constitute compositions which mimic seawater. However, these are not exact replica of seawater and in that sense they are non-standard compositions which vary from formulation to formulation. The only thing that appears to be common to all is their prohibitive cost which further limits the scope of such seawater applications in locations not blessed with a coast line.

Fresh water is what we drink and also use for agriculture. In many instances the water is severely deficient in nutritious minerals, particularly the water obtained from desalination plants. Indeed, it is unfortunate that the desalination process not only drives out sodium chloride but also essential minerals and in cases such as reverse osmosis based desalination, these are preferentially driven out making a bad situation worse. Although the problem can be mitigated through re-mineralization, many plants do not practice re-mineralisation due to the additional cost involved, particularly the high cost of the nutrient salts.

Reference may be made to the article entitled "Elemental composition of commercial sea salts" by M. J. Atkinson and C. Bingham (Journal of Aquaculture and Aquatic Sciences, 1997, Volume VIII, No. 2, Page 39-43) in which it is reported that eight different commercially available synthetic sea salt mixes were analyzed for some thirty-five elements and ions and other chemical parameters. Although the major cations and anions were within 10% of seawater in most of the salts, there were significant differences in the amounts of the minor constituents. It was found that "total $CO_2$ varies about 20 times, B varies about 13 times from 0.36 to 4.90 mmol $kg^{-1}$, phosphate concentrations vary 24 fold from extremely low values of 0.05 μmol $kg^{-1}$ to moderate concentrations of 1.2 μmol $kg^{-1}$, nitrate varies from 0.79 to 18.4 μmol $kg^{-1}$, and most transition metals are present in substantially higher concentrations compared to normal seawater. It is therefore apparent that none of the salts studied can be assumed to be natural salt compositions mimicking a dried sea.

Reference may be made to http://web.archive.org/web/20001215070800/http:/www.animalnetwork.com/fish2/aqfm/1999/mar/features/1/default.asp, different sources of brine as listed in the following table from which artificial seawater can be produced in the solid form. Most of these compositions are silent on the essential trace elements present in seawater. Another drawback of these sources is that these products having the cited compositions are invariably expensive. They are available in a price range of 45-70 USD per 150-200 gallons of seawater which works out to a premium cost of Rs. 2/liter than that of natural sea water.

TABLE 1

The Composition of Several Synthetic Seawater Mixes

| Commercial Name | Salinity (ppt) | Na | Mg | Ca | K | Sr | Cl— | SO4— | BO3 | HCO3—CO3— |
|---|---|---|---|---|---|---|---|---|---|---|
| Seawater | 35 | 470 | 53 | 10.3 | 10.2 | 0.09 | 550 | 28 | 0.42 | 1.90 |
| Instant Ocean | 29.65 | 462 | 52 | 9.0 | 9.4 | 0.19 | 521 | 23 | 0.44 | 1.90 |
| Tropic Marine | 32.64 | 442 | 46 | 8.9 | 9.1 | 0.08 | 497 | 21 | 0.36 | 1.10 |
| HW Marine Mix | 29.40 | 467 | 53 | 9.0 | 10.1 | 0.15 | 538 | 28 | 0.41 | 2.10 |
| Reef Crystals | 28.91 | 461 | 50 | 9.3 | 9.5 | 0.08 | 520 | 27 | 0.65 | 0.75 |
| Red Sea Salt | 30.07 | 472 | 55 | 9.0 | 9.9 | 0.10 | 537 | 25 | 0.54 | 1.08 |
| Kent | 28.85 | 460 | 57 | 10.4 | 10.1 | 0.10 | 531 | 24 | 0.54 | 2.52 |
| Coralife | 28.39 | 464 | 63 | 10.1 | 9.3 | 0.08 | 566 | 15 | 1.26 | .32 |
| Sea Chem | 29.54 | 504 | 37 | 10.1 | 10.7 | 0.21 | 516 | 37 | 4.90 | .12 | ppt = parts per thousand

Reference may be made to US 2005/0193956 dated: Aug. 9, 2005 Axelrod, Glen S. et al discloses a process for the preparation of a synthetic ocean salt comprising the mixing of Sodium Chloride 50-55% (wt) Magnesium Chloride 30-32% (wt) Anhydrous Sodium Sulphate 7-10% (wt) Calcium Chloride 2-4% (wt) Potassium Chloride 2-4% (wt) Sodium Bicarbonate 0.1-1% (wt) Boric Acid 0.001-0.010% (wt). The invention reports the preparation of a synthetic ocean mix from pure chemicals.

Reference may also be made to an article entitled "Guidance from Secondary Data for Re-mineralisation of RO Water" by Srivastava et al (Journal of Indian Water Works Association, January-March 2010 issue, pp. 50-52) which discusses ideal water compositions for potable purposes. The need for remineralisation of such desalinated water is evident from the article.

References may be made to an article by Gordon Sato et al (*Cytotechnology* (2011) 63:201-204) and many other articles in the prior art which disclose the well known use of media such as Zobell marine broth and ASNIII for culturing of marine microbes.

In view of the above there is a need for the invention of inexpensive, effective and uniform salt compositions to cater to the needs as described above.

OBJECTS OF INVENTION

The main object of the present invention is to develop a process for the preparation of natural salt formulations for seawater substitution, mineral fortification.

Another object of the present invention is to provide natural salt formulations from seawater which are inexpensive and yet efficacious in their assigned tasks.

Another object of the present invention is to convert sea water into dry form using solar energy.

Yet another object of the present invention is to utilize seawater from pristine locations free of contamination.

Yet another object of the present invention is to fractionate seawater into three broad compositions which can be used either singly or in combination.

Yet another object of the present invention is to enable consumers to have the benefit of greater flexibility of use than possible with seawater itself or with the commercial formulations.

Yet another object of the present invention is to show that marine microalgae grow just as well in seawater prepared with Dry Sea as in natural seawater.

Yet another object of the present invention is to show that halophilic bacteria (*Halomonas*, and *Pseudomonas* spp.) grow well in seawater prepared from Dry Sea as in natural seawater.

Yet another object of the present invention is to improve the characteristics of natural seawater by increasing or decreasing the TDS suitably varying the proportions of Dry Sea—MF.

Yet another object of the present invention is to formulate an ideal salt mixture largely free of NaCl in seawater, but otherwise having all the other constituents, which can be utilised for re-mineralisation of low TDS water for production of healthy mineral-fortified potable water and irrigation water.

Yet another object of the present invention is to produce these formulations at a meagre cost compared to cost entailed in the use of commercially available salts.

Yet another object of the present invention is to produce such salts in solar pans free of percolation so that all constituents are maintained intact.

Yet another object of the present invention is to obtain salt formulations that are free of mud and dust.

Yet another object of the present invention is to undertake the preparation of the salts under controlled conditions for its manifold applications.

SUMMARY OF THE PRESENT INVENTION

Accordingly, the present invention provides a process for the preparation of natural salt formulation, wherein the said process comprising the steps of;
a) collection of sea brine of 2.5-4.0° Bé
b) subjecting the sea brine as obtained in step (a) to solar evaporation till 25° Bé density to obtain a salt composition of fraction I which is substantially free of sodium chloride and contains calcium, sulphate and carbonate/bicarbonate as the main constituents, and a brine rich in sodium chloride and other constituents;
c) feeding the resultant brine of step (b) into another crystallizing pan and continuing solar evaporation of the saturated brine till the density reaches 28.5-31.0° Bé density to separate out much of the sodium chloride in seawater as fraction II, without being particularly concerned about the purity of sodium chloride, and leaving a mother liquor bittern largely free of NaCl;
d) harvesting the salt as obtained in step (c) in the open sun;
e) feeding the mother liquor bittern as obtained in step (c) into another crystallizing pan and continuing solar evaporation to close to solidification stage to obtain fraction III;
f) harvesting the salts crystallized as obtained in step (e);
g) mixing the fractions (I), (II) and (III) as obtained in step (b), (d) and (f) in the proportions in which these are obtained to produce a natural salt formulation mimicking a dry sea.
h) mixing only the fractions (I) and (III) in ratio ranging between 1:3 to 1:6 to obtain natural salt formulations which are substantially free of sodium chloride while containing other constituents in the seawater, particularly calcium, magnesium, potassium, carbonate/bicarbonate, sulphate and micronutrients;

In one embodiment of the invention, the sea brine as obtained in step (a) was clarified through flocculation or ordinary filtration or preferably ultrafiltration to separate out suspended matter including cysts, spores and microbes prior to charging into pans for evaporation in step (b).

In another embodiment of the invention, the salt composition of fraction I recovered in step (b) having a free moisture content of 3-5% (w/w) was optionally added into the mother liquor of step (e) prior to further evaporation to soak in some of the moisture, and in the process reducing to some extent the evaporation load while still obtaining a product which is dry to handle.

In yet another embodiment, natural salt formulation as obtained in step (g) was used for reconstitution of sea water by re-dissolving of salts into fresh water sources.

In still another embodiment, use of natural crude salt fractions isolated from the sea brine towards cost-effective reconstitution of seawater and mineral fortification, said fractions having the compositions as follows:
(i) fraction I containing much of the calcium, bicarbonate/carbonate and a part of the sulphate in seawater, and comprising $Ca^{2+}$=20-23% (w/w), $Mg^{2+}$=0.05-0.2% (w/w), $Na^+$=0.75-1.5% (w/w), $SO_4^{2-}$=48-54% (w/w), $Cl^-$=2.3-3% (w/w), along with small amounts of $CO_3^{2-}/HCO_3^-$ whose absolute amount varies depending on $CO_2$ concentration and pH, and traces of other constituents present in seawater which may get co-crystallized or occluded or remain from adhering brine;
(ii) fraction II consisting essentially of sodium chloride in the seawater separated out with an eye on minimizing the NaCl content in fractions I and III and without being particularly concerned about the purity of the NaCl;
(iii) fraction III which has useful constituents such as magnesium, sulphate and potassium while excluding much of the sodium chloride in seawater, and comprising $Ca^{2+}$=0.08-4.15% (w/w), $Mg^{2+}$=11-15% (w/w), $Na^+$=3-6% (w/w), $SO_4^{2-}$=16-19.5% (w/w), $Cl^-$=38-40% (w/w), $K^+$=3.5-4.5%(w/w).

In still another embodiment, use of natural crude salt fractions isolated from the sea brine for fortification of mineral-deficient water, wherein mixing of fractions (I) and (III) was carried out in ratio ranging between 1:3 to 1:6.

In still another embodiment use of natural crude salt fractions isolated from the sea brine for reconstitution of seawater, wherein mixing of fractions (I), (II) and (III) was carried out in the same weight proportions as in which they were obtained.

In still another embodiment, the natural salt formulation was useful for the survival and growth of marine fauna and flora in an aquarium.

In still another embodiment, the natural salt formulation was useful for the growth of marine bacteria and microalgae and is useful as a substitute for ordinary seawater or special media such as Zobell marine broth and ASNIII medium.

In still another embodiment, the salinity of the seawater is made to vary as desired by varying the amount of the salt which is added.

In still another embodiment, the natural salt formulations obtained can be used for fortification of mineral-deficient water having 10-250 mg·L$^1$ total dissolved solids to give nutritious water having 300-500 ppm total dissolved solids, with desired amounts of calcium, magnesium, potassium, bicarbonate and sulphate, and low levels of sodium chloride as prescribed in various standards for potable and irrigation water.

In still another embodiment, the the sea brine is continuously evaporated without fractionation to obtain similar salt formulation as claimed in step (g) of claim 1.

In still another embodiment, evaporation of the sea brine can be undertaken under more controlled conditions employing forced evaporation methods in part or in full.

In still another embodiment, re-dissolution of the salts in water was accelerated by known means as increasing surface, heating, subjecting to microwave treatment.

In still another embodiment, solutions of the salts are filtered to remove coarse and finely suspended matter prior to use.

In an embodiment of the present invention the brine used for the preparation of Dry Sea—MF is sea water.

In yet another embodiment of the present invention the salt fractions separated at different stages can be mixed in different prepositions to get desired composition for its specific application.

In yet another embodiment of the present invention the Dry Sea—MF is obtained under ambient conditions.

In yet another embodiment of the present invention the media prepared from Dry Sea gives the same results as that of sea water in culture of marine microbes/fish.

In yet another embodiment of the present invention the Dry Sea—MF can be utilized for the fortification of RO/ED desalinated water to get potable water.

In yet another embodiment of the present invention the Dry Sea produced is superior to the synthetic sea mix available in the commercial market.

In yet another embodiment of the present invention the Dry Sea can be used in marine aquarium in place of natural sea water.

In yet another embodiment of the present invention the salt formulations are cost effective and can be produced in any solar salt works.

ABBREVIATIONS & DEFINITIONS

TDS: Total Dissolved Solids
ASN III: Artificial Seawater Nutrient Medium
Degree Baume: Throughout the specification, the density of brine is defined in terms of sup.° Bé which is a convenient and widely used scale for measuring brine density in solar salt works. It gives a direct measure of the quantity of salt dissolved in 100 g of solution. In American systems, degree Baume is related to the specific gravity by the equation:

Specific gravity=145/(145−sup. °$Bé$).

BRIEF DESCRIPTION OF THE DRAWINGS

FIG. 1: Comparison of growth profiles of *Chlorella variabilis* in regular sea water and the seawater medium prepared by the present invention.

FIG. 2: Comparison of growth profiles of *Chlorella variabilis* grown in Dry Sea medium vs. Zarrouk's medium in a raceway pond with working volume of 150 L.

FIG. 3: Growth rate of *Spirulina subsalsa* under ASN III medium and Dry Sea water condition.

FIG. 4: Growth rate of *Bacillus licheniformis* in Zobell marine broth and Dry Sea water condition.

DETAILED DESCRIPTION OF THE PRESENT INVENTION

Figure 1:
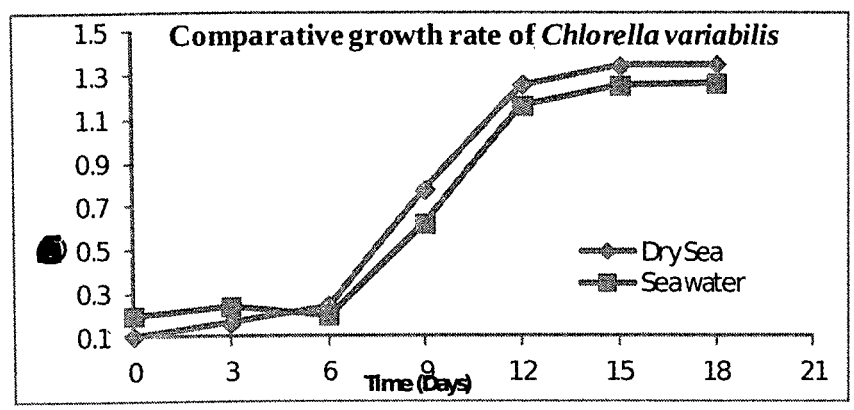
FIG. 1 to 4 demonstrates the similar growth trends in natural seawater medium and medium prepared from Dry Sea.
Figure 2:
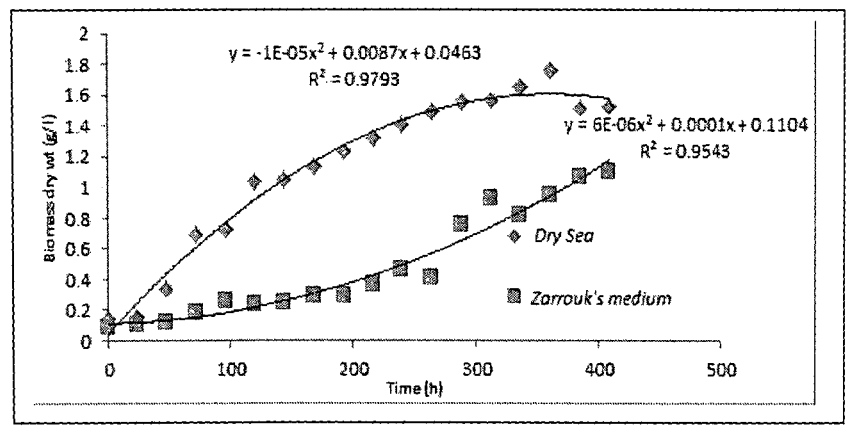

The present invention relates to a cost-effective natural salt formulations as seawater substitute for various operations such as marine aquarium, culture media for a wide variety of marine micro algae, agriculture, mineral fortification etc.

Seawater is collected and charged into lined solar pans. It is evaporated till the brine attains 25° Bé and salts crystallized till that point, mainly carbonate/bicarbonate and sulphate salts of calcium are separated. The brine is thereafter charged into another solar pan and evaporation continued till 28-29° Bé whereupon majority of the sodium chloride present in the brine is crystallized out. After the separation of sodium chloride crystals, the mother liquor termed as bittern is charged into a third solar pan and evaporated close to solidification stage and the magnesium/potassium salts and the left over sodium chloride is collected. The contents from all the three pans are thoroughly mixed to yield Dry Sea containing all of the constituents originally present in seawater.

In a variation of the above process, the second fraction comprising predominantly NaCl is discarded while a part of the third fraction (bittern) is mixed with the salts obtained in the first fraction and evaporated till the mass is solidified completely. The solids are then crushed and mixed to obtain a uniform composition (designated as Dry Sea—MF) enriched in calcium, magnesium, potassium, bicarbonate/carbonate and sulphate. The proportions of the two fractions are varied as required in different applications. Further, by avoiding the NaCl fraction, new application opportunities emerge such as mineral fortification of Desalinated water.

The present invention provides cost-effective natural salt formulations prepared from natural sea water as a seawater substitute for various applications comprising the steps of:
 a) collection of sea brine of 2.5-4.0° Bé
 b) subjecting sea brine to evaporate till 25° Bé density;
 c) collection of salts crystallized till 25° Bé density;
 d) feeding the brine of (b) into another crystallizing pan and continuing solar evaporation of the saturated brine to crystallize out salt till 27-28.5° Bé density;
 e) draining out the mother liquor from the crystallizing pan;
 f) harvesting the salt in the open sun;
 g) feeding the mother liquor of (e) into another crystallizing pan and continuing solar evaporation to close to solidification stage;
 h) harvesting the salts crystallized in step (g).

Inventive Steps

The main inventive steps are:
Recognizing that seawater is not available in the regions located far off from the coastal belts and yet seawater may be required in these regions for specific purposes such as conducting research, maintaining marine aquariums, growing marine algae, etc.

Further recognizing that such need for seawater are difficult to meet due to the high cost of transporting seawater and formulating seawater from the costly synthetic salt compositions available in the market.

Further recognizing that even if synthetic salt formulations can be afforded by certain users, these may not necessarily instill confidence in the minds of users as they are not sure whether these contain all of the minor constituents present in seawater in addition to the major constituents, and whether they will get seawater for sure.

Conceptualizing thereafter that if seawater can be dried completely and if subsequently the salts are re-dissolved in fresh water, one would get the same seawater back.

Further recognizing that salt production entails near complete drying of seawater and one may take advantage of the prior art to devise means of obtaining suitable salt formulations for the stated objective.

Further recognizing that if fractional crystallization is undertaken, then the salts can be collected in three broad fractions, one of which is the predominant constituent, namely sodium chloride, and which can be excluded from formulations to be used for mineral fortification.

Further recognizing that since the goal is to separate out as much of the sodium chloride as possible in the fraction II and not the production of pure sodium chloride, and thereafter focusing on maximizing the separation of sodium chloride without worrying about the fact that this act would make the sodium chloride more impure in the process.

Further recognizing that if these three constituents are mixed in exactly the same weight proportions in which they are obtained, and if the total dissolved solids are maintained the same as in initial seawater, then one would have reconstituted seawater exactly.

Further recognizing that if the major constituent is excluded and the other two fractions blended, then the blend can serve as a rich source of calcium, magnesium, potassium, sulphate and bicarbonate, all of which are essential constituents which should be present in potable water within a range and also in agricultural water up to certain limits.

Recognising further that in many cases the water we drink, including desalinated water, is device of essential nutrients and that re-mineralization is sometimes not undertaken due to the high cost of the salts, and recognizing further that salts obtained in crude form rather than in pure form are always less expensive to produce.

Recognising that there are reports of mineral deficiency in the case of agriculture water also and that such waters too may need mineral fortification.

Recognising fractions I and III can be utilized for mineral fortification either singly or blended in appropriate ratios depending on the application and state of feed water.

the Following Examples are Given by Way of Illustration of the Present Invention and Therefore should not be Construed to Limit the Scope of the Present Invention.

EXAMPLE 1

10 cu. M. of Seawater (7.2° Bé) having the composition $Ca^{2+}=0.1\%$ (w/v), $Mg^{2+}=0.27\%$ (w/v) $Na^+=2.3\%$ (w/v), $SO_4^{2-}=0.54\%$ (w/v), $Cl^-=4.1\%$ (w/v), $K^+=0.08\%$ (w/v) was transferred to two pans having identical size of 12 M.×2 M.×0.23 M each. The pans were lined with 250 micron LDPE sheet. The seawater was subjected to solar evaporation up to 25° Bé.

a. At 25° Bé 48 kg of salts having composition $Ca^{2+}=20.02\%$ (w/w), $Mg^{2+}=0.37\%$ (w/w) $Na^+=1.1\%$ (w/w), $SO_4^{2-}=52.27\%$ (w/w), $Cl^-=2.97\%$ (w/w), $K=$traces was separated a Fraction—I.

b. The saturated brine of 25° Bé was transferred to another Pan of same size lined with LDPE sheet and subjected to solar evaporation till 28.5° Bé. 545 kg of salt having the composition $Ca^{2+}=0.1\%$ (w/w), $Mg^{2+}=0.35\%$ (w/w), $Na^+=38.6\%$ (w/w), $SO_4^{2-}=0.62\%$ (w/w), $Cl^-=59.3\%$ (w/w), $K^+=$traces was crystallized in the second pan and was collected as Fraction—II.

c. The mother liquor having a density of 28.5° Bé was transferred to a third solar Pan of same size and mixed with Fraction—I separated in step (a) and was evaporated to complete dryness stage. At this point a quantity of 220 kg of salt mixture having a composition $Ca^{2+}=4.15\%$ (w/w), $Mg^{2+}=11.4\%$ (w/w), $Na^+=5.8\%$ (w/w), $SO_4^{2-}=22.7\%$ (w/w), $Cl^-=39.1\%$ (w/w) and $K^+=3.8\%$ (w/w) was collected as mixed Fraction—III. The salt composition obtained in this manner is referred to as Dry Sea-MF.

EXAMPLE 2

5 cu. M. of Seawater of 2.9° Bé density having $Ca^{2+}=0.03\%$ (w/v), $Mg^{2++}=0.11\%$ (w/v), $Na^+=0.88\%$ (w/v), $K^+=0.03\%$ (w/v), $SO_4^{2-}=0.22\%$ (w/v) and $Cl^-=1.58\%$ (w/v), was transferred to 12 M.×2 M×0.23 M size solar pan lined with 250 micron LDPE sheet and allowed to evaporate upto 25° Bé.

a. At 25° Bé, 6 kg of salts having composition $Ca^{2+}=21.0\%$ (w/w), $Mg^{2+}=0.08\%$ (w/w), $Na^+=1.1\%$ (w/w), $SO_4^{2-}=52.5\%$ (w/w), $Cl^-=2.8\%$ (w/w), $K^+=$traces was harvested as Fraction—I.

b. This saturated brine (25° Bé) transferred another Pan of same size (12 M.×2 M.×0.23 M.) lined with LDPE sheet. The saturated sea brine of 25° Bé was allowed to evaporate till 28.5° Bé and 110 kg of salt having composition $Ca^{2+}=0.18\%$ (w/w), $Mg^{2+}=0.37\%$ (w/w), $Na^+=38.6\%$ (w/w), $SO_4^{2-}=0.62\%$ (w/w), $Cl^-=59.3\%$ (w/w), $K^+=$traces was obtained as Fraction—II.

c. The sea bittern of 28.5° Bé density left after the separation of fraction II was transferred to another solar pan of same size and allowed for complete evaporation. 35 kg of salt having the composition $Ca^{2+}=0.11\%$ (w/w), $Mg^{2+}=14.4\%$ (w/w), $Na^+=4.2\%$ (w/w), $SO_4^{2-1}=18.58\%$ (w/w), $Cl^-=38.28\%$ (w/w), $K^+=4.2\%$ (w/w) was obtained as Fraction—III.

d. Fraction I and III was mixed in toto (1:5.83), to obtain natural salt formulations which are substantially free of sodium chloride while containing other constituents in the seawater such as, calcium, magnesium, potassium, carbonate/bicarbonate, sulphate and micronutrients. It was observed that the weight ratio varies with the moisture content of the respective fractions.

EXAMPLE 3

5 cu. M. of Seawater of 4.22° Bé density having $Ca^{2+}=0.05\%$ (w/v), $Mg^{2+}=0.15\%$ (w/v), $Na^+=1.3\%$ (w/v), $SO_4^{2-}=0.3\%$ (w/v), $Cl^-=2.35\%$ (w/v), $K^+=0.047\%$ (w/v) was transferred to 12 M.×2 M.×0.23 M Size Pan duly lined with 250 micron LDPE sheet.

a. The seawater was allowed to evaporate upto 25° Bé. 11 kg of salts having composition $Ca^{2-}=21.9\%$ (w/w), $Mg^{2+}=0.08\%$ (w/w), $Na^+=1.1\%$ (w/w), $SO_4^{2-}=51.5\%$ (w/w), $Cl^-=2.89\%$ (w/w), $K^+=$traces was harvested as Fraction—I.

b. This saturated brine (25° Bé) transferred another Pan of same size (12 M.×2 M.×0.23 M.) lined with LDPE sheet. The saturated sea brine of 25° Bé allowed for evaporation till 28.5° Bé. The bittern having density of 28.5° Bé was transferred to previous Pan and 160 kg of salt having composition $Ca^{2+}=0.15\%$ (w/w), $Mg^{2+}=0.37\%$ (w/w), $Na^+=38.6\%$ (w/w), $SO_4^{2-}=0.62\%$ (w/w), $Cl^-=59.3\%$ (w/w), $K^+$=traces was obtained as Fraction—II.

c. The sea bittern (28.5° Bé density) was transferred in another pan and allowed for complete evaporation. At close to complete evaporation the salt was having moisture i.e. bitterns. A this point, quantity 47.7 kg of salts having composition $Ca^{2+}=0.11\%$ (w/w), $Mg^{2+}=14.4\%$ (w/w), $Na^-=6.2\%$ (w/w), $SO_4^{2-}=17.5\%$ (w/w), $Cl^-=40.04\%$ (w/w), $K^+=4.2\%$ (w/w) was obtained as Fraction—III.

d. Fraction I and III was mixed in toto (1:4.33), to obtain natural salt formulations which are substantially free of sodium chloride while containing other constituents in the seawater such as, calcium, magnesium, potassium, carbonate/bicarbonate, sulphate and micronutrients. It was observed that the weight ratio varies with the moisture content of the respective fractions.

Since the fractionation process of the present invention is conducted to separate out the bulk of NaCl in seawater as one of the objectives, without being concerned about the purity of that NaCl the evaporation process in step (b) can be optionally continued all the way up to 31° Bé so as to separate out a still higher percentage of the NaCl in seawater and leave mother liquor bittern with lower levels of NaCl so as to obtain a salt composition in fraction 3 which is still lower in NaCl. Fraction II in that case has the composition $Ca^{2+}=0.1\%$ (w/w), $Mg^{2+}=1.0\%$ (w/w), $Na^+=36\%$ (w/w), $SO_4^{2-}=2.4\%$ (w/w), $Cl^-=57.7\%$ (w/w), $K^+=0.01\%$ (w/w) with a free moisture content of 3-5% (w/w). This would be especially beneficial for the purpose of producing Dry Sea MF which is largely devoid of NaCl while making no difference in the composition of Dry Sea.

EXAMPLE 4

The NaCl fraction obtained in step (b) of Example 1 was mixed with Dry Sea MF obtained in step (c) in the proportion 545:220=2.46:1 and the mixed composition is referred to as Dry Sea. 32 gm of Dry Sea was added per liter of tap water and several liters of the water were prepare simulating seawater salinity. 500 ml of this water was autoclaved at 121° C. for 20 minutes. TI medium was inoculated with 10% of an inoculum of *Chlorella variabilis* marine microalga (ATC Accession No. PTA-12198) having optical density of 0.8-1.0 at 540 nm. The flask was kept in static condition at 30° C. The growth parameter was monitored through optical density measurements at 540 nm wavelength at regular intervals. The growth of the micro alga in regular sea water and the seawater medium prepared above was studied and a plot of the data is provide in FIG. 1. The results show similar growth trend in both the media.

EXAMPLE 5

Growth of *Chlorella variabilis* of Example 4 was studied in a raceway pond constructed in location far away from source of natural seawater. Seawater prepared from the salt fraction obtained in Example 2 was used for this purpose and conventionally used Zarrouks medium use normally in these situations served as the control. Dry Sea was constituted from the salt fraction a, b and c of example 2, these salts being mixed in the same weight proportions as in which the were obtained, i.e., 6:110:35. Seawater was prepared by dissolving 525 g of this Dry Sea sa formulation in 150 L of normal tap water available in that area to give ~3.5% (w/v) solids similar to seawater concentration and composition. The microalga was cultivated firstly in the define Zarrouk's medium and secondly in the seawater medium constituted from Dry Sea. The size of the inocula were 10%(v/v) in both the cases. Inoculation was done at a pH value of 10 for Zarrouk medium and at pH 7.6 for the Dry Sea medium, and the details of the culturing conditions are given in Table 2. The growth was monitored periodically and the data are presented in Figure below. Besides obtaining a better growth profile in Dry Sea medium, this medium also helped is settling the biomass which facilitated harvesting.

TABLE 2

| Culturing conditions maintained during growth profile study | | | | | |
|---|---|---|---|---|---|
| Strain | Medium | pH | Light intensity (Lux) | Temp. (° C.) | Photoperiod |
| *Chlorella variabilis* | Zarrouk's Dry Sea | 10 7.6 | 40000-60000 | 35-40 | 14:10 |

EXAMPLE 6

Figure 3:
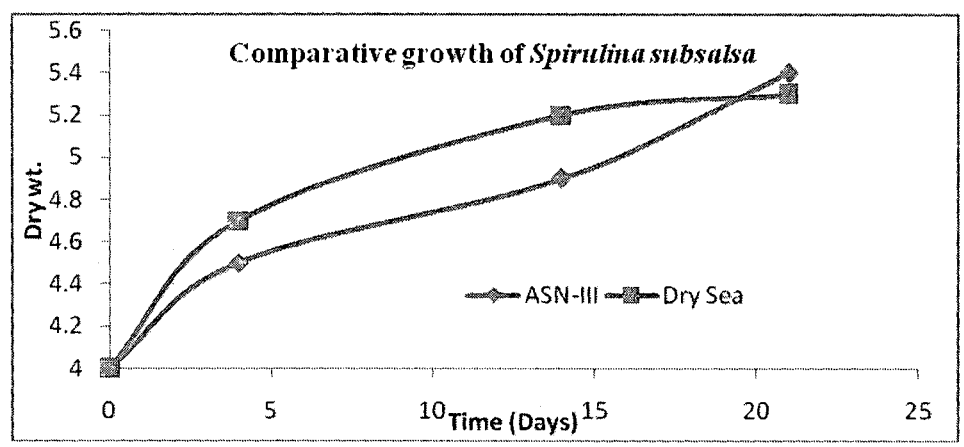

Seawater prepared as in Example 5 was utilised as the culture medium for observing the growth of marine *Spirulina subsalsa* under laboratory conditions. Studies were conducted with full strength of seawater (32.19 g/l) and also with half (~16 g/l) and quarter (~8 g/l) strengths. ASNIII (artificial seawater nutrient medium) medium was used as control. Cultures grown in the lower concentrations of salts showed much less growth whereas culture having 32.19 g/l Dry Sea showed good growth, and at this concentration the results were quite comparable to that of growth in the control medium as shown in FIG. 3.

Examples 4-6 teach us that Dry Sea can serve as a natural formulation for constitution of seawater useful for growth of marine microalgae.

EXAMPLE 7

Figure 4:
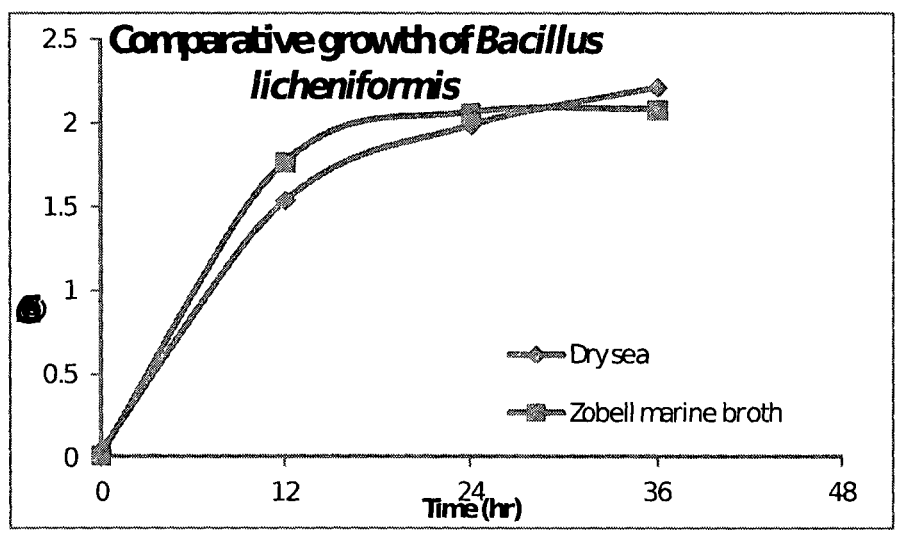

Seawater was reconstituted from the salt fractions of Example 3 and utilised as the culture medium for observing the growth of *Bacillus licheniformis* (MTCC 5549) marine bacteria, Two separate media, one with 100 ml of Zobell marine broth & the second with 100 ml of reconstituted seawater (Dry Sea) were prepared with 5 gm/l peptone and 1 gm/l yeast extract. The media taken in 500 ml Erlenmeyer flasks were sterilized at 121° C. for 20 minutes and thereafter inoculated with 1 ml of 24 hour old culture of the said bacteria. The flasks were kept in an orbital shaker at 150 rpm/32° C. Optical density of cultures was monitored at regular intervals for a period of 36 hours. Comparative data on the growth of the bacteria in Zobell marine broth and Dry Sea media are graphically presented in FIG. 4. The results show similar growth trend in both the media.

Example 7 teaches us that Dry Sea can serve as a natural formulation for constitution of seawater useful for growth of marine bacteria.

EXAMPLE 8

Seawater prepared as in Example 4 was poured in a marine aquarium of dimensions: Length=3 ft, Width=1 ft 6", and Height=2 ft. And marines fishes such as Star fish, Tiger fish, Sea Anemone and Clown fish were taken in the aquarium. The report received from the individual who conducted the study states that "the sea water fishes seem to be very comfortable in the water since last two months".

Example 8 teaches us that Dry Sea can serve as a natural formulation for constitution of seawater useful for application in marine aquariums.

EXAMPLE 9

In this example, Dry Sea—MF of Example 1 was used for the re-mineralisation of ca. 35 ppm TDS desalinated water obtained from an Electro dialysis-Reverse Osmosis hybrid domestic desalination unit. Remineralized water having a TDS of 450 ppm was obtained having the composition a indicated in Table 3. The remineralized water had only 160 ppm of NaCl and significant amount of useful constituents such as calcium, magnesium, sulphate and bicarbonate. Such remineralize water would be useful both for drinking and agricultural applications.

TABLE 3

| Constituents | Concentration in ppm | Method of analysis |
|---|---|---|
| Ca | 52.17 | ICP-AAS |
| K | 1.53 | ICP-AAS |
| Mg | 39.57 | ICP-AAS |
| Na | 64.12 | ICP-AAS |
| Cl | 149.1 | Titration |
| $HCO_3$ | 98.0 | Titration |
| $SO_4$ | 48.0 | Titration |
| As | Below Detection Level | ICP-AAS |
| Cd | Below Detection Level | ICP-AAS |
| Hg | Below Detection Level | ICP-AAS |
| Pb | Below Detection Level | ICP-AAS |

Example 9 teaches us that Dry Sea-MF can serve as a cost-effective and natural formulation for remineralization of low TDS water, including desalinated water.

The main advantages of the present invention are:

Seawater is fractionated by solar evaporation to obtain three crude compositions of salt and, consequently, the process is very cost effective.

Not only the major constituents but even trace constituents in seawater are retained in on or more of the fractions.

The process is entirely natural, free of effluent, and does not involve handling of any synthetic chemicals.

The solid salt fractions or their suitable blends can be transported cost effectively.

Sea water can be made available in its pristine form in any part of the globe where see water is not available in the vicinity but there is availability of fresh water.

A salt composition substantially free of sodium chloride can also be constituted which would have utility for cost-effective mineral fortification.

We claim:

1. A process for the preparation of natural salt formulation, wherein the process comprises the steps of:
   (a) collection of sea brine of 2.5-4.0° Bé;
   (b) subjecting sea brine as obtained in step (a) to solar evaporation till 25° Bé density to obtain salt composition of fraction I which is substantially free of sodium chloride and contains calcium, sulphate and carbonate/bicarbonate as the main constituents, and a brine rich in sodium chloride and other constituents;
   (c) feeding the resultant brine of step (b) into another crystallizing pan and continuing solar evaporation of the saturated brine till the density reaches 28.5-31.0° Bé density to separate out much of the sodium chloride in the sea brine as fraction II, without being particularly concerned about the purity of sodium chloride, and leaving a mother liquor bittern largely free of NaCl;
   (d) harvesting the salt as obtained in step (c) in the open sun;
   (e) feeding the mother liquor bittern as obtained in step (c) into another crystallizing pan and continuing solar evaporation to close to solidification stage to obtain fraction III;
   (f) harvesting the salts crystallized as obtained in step (e); and
   (g) mixing the fractions (I), (II) and (III) as obtained in step (b), (d) and (f) in the proportions in which these are obtained to produce a natural salt formulation mimicking a dry sea or optionally;
   (h) mixing only the fractions (I) and (III) in ratio ranging between 1:3 to 1:6 to obtain natural salt formulations which are substantially free of sodium chloride while containing other constituents in the sea brine, particularly calcium, magnesium, potassium, carbonate/bicarbonate, sulphate and micronutrients.

2. The process as claimed in claim 1, wherein the sea brine as obtained in step (a) of claim 1 was clarified through flocculation or ordinary filtration or preferably ultrafiltration to separate out suspended matter including cysts, spores and microbes prior to charging into pans for evaporation in step (b).

3. The process as claimed in claim 1, wherein the salt composition of fraction I recovered in step (b) having a free moisture content of 3-5% (w/w) was optionally added into the mother liquor of step (e) prior to further evaporation to soak in some of the moisture, and in the process reducing to some extent the evaporation load while still obtaining a product which is dry to handle.

4. The process as claimed in claim 1, wherein natural salt formulation as obtained in step (g) of claim 1, was used for reconstitution of sea water by re-dissolving of salts into fresh water sources.

5. The process as claimed in claim 4, wherein the natural salt formulation is useful for the survival and growth of marine fauna and flora in an aquarium.

6. The process as claimed in claim 4, wherein the natural salt formulation is useful for the growth of marine bacteria and microalgae and is useful as a substitute for ordinary seawater or special media such as Zobell marine broth and ASNIII medium.

7. The process as claimed in claim 4, wherein the salinity of the seawater is made to vary as desired by varying the amount of the salt which is added.

8. The process as claimed in claim 1, wherein the natural salt formulations obtained in step (h) are used for fortification of mineral-deficient water having 10-250 mg·L-1 total dissolved solids to give nutritious water having 300-500 ppm total dissolved solids, with desired amounts of calcium, magnesium, potassium, bicarbonate and sulphate, and low levels of sodium chloride as prescribed in various standards for potable and irrigation water.

9. The process as claimed in claim 1, wherein evaporation of the sea brine can be undertaken under more controlled conditions employing forced evaporation methods in part or in full.

10. The process as claimed in claim 1, wherein re-dissolution of the salts in water was accelerated by increasing surface, heating, subjecting to microwave treatment.

11. The process as claimed in claim 1, wherein solutions of the salts are filtered to remove coarse and finely suspended matter prior to use.

12. A method for the use of natural crude salt fractions isolated from sea brine towards cost-effective reconstitution of seawater and mineral fortification, said fractions having the compositions as follows:

1. fraction I containing much of the calcium, bicarbonate/carbonate and a part of the sulphate in sea brine, and comprising $Ca^{2+}$=20-23% (w/w), $Mg^{2+}$=0.05-0.2% (w/w), $Na^+$=0.75-1.5% (w/w), $SO_4^{2-}$=48-54% (w/w), $Cl^-$=2.3-3% (w/w), along with small amounts of $CO_3^{2-}/HCO_3^-$ whose absolute amount varies depending on $CO_2$ concentration and pH, and traces of other constituents present in sea brine which may get co-crystallized or occluded or remain from adhering brine;
2. fraction II consisting essentially of sodium chloride in the sea brine separated out with an eye on minimizing the NaCl content in fractions I and III and without being particularly concerned about the purity of the NaCl;
3. fraction III which has useful constituents such as magnesium, sulphate and potassium while excluding much of the sodium chloride in seawater, and comprising $Ca^{2+}$=0.08-4.15% (w/w), $Mg^{2+}$=11-15% (w/w), $Na^+$=3-6% (w/w), $SO_4^{2-}$=16-19.5% (w/w), $Cl^-$=38-40% (w/w), $K^+$=3.5-4.5%(w/w).

13. The method for the use of natural crude salt fractions isolated from sea brine as claimed in claim 12 for fortification of mineral-deficient water, wherein mixing of fractions (I) and (III) was carried out in ratio ranging between 1:3 to 1:6.

14. The method for the use of natural crude salt fractions isolated from seawater as claimed in claim 12 for reconstitution of seawater, wherein mixing of fractions (I), II and (III) was carried out in the same weight proportions as in which they were obtained in steps (b), (d) and (f) respectively of claim 1.

* * * * *